(12) United States Patent
McMichael et al.

(10) Patent No.: US 6,989,368 B2
(45) Date of Patent: Jan. 24, 2006

(54) USE OF CALMODULIN TO PROMOTE BONE REGENERATION

(75) Inventors: John McMichael, Delanson, NY (US); Harry C. Gurney, Evergreen, CO (US)

(73) Assignee: Milkhaus Laboratory, Inc., Provindence, RI (US)

( * ) Notice: Subject to any disclaimer, the term of this patent is extended or adjusted under 35 U.S.C. 154(b) by 177 days.

(21) Appl. No.: 10/330,667

(22) Filed: Dec. 27, 2002

(65) Prior Publication Data

US 2003/0232751 A1   Dec. 18, 2003

Related U.S. Application Data

(60) Provisional application No. 60/349,163, filed on Jan. 16, 2002.

(51) Int. Cl.
*A61K 9/00* (2006.01)
*A61K 38/00* (2006.01)
*A61K 31/28* (2006.01)

(52) U.S. Cl. .............................. 514/12; 514/8; 514/21; 514/492; 424/650

(58) Field of Classification Search ................ 424/400, 424/650; 514/12, 8, 492, 21
See application file for complete search history.

(56) References Cited

U.S. PATENT DOCUMENTS

| 5,698,518 A | 12/1997 | Carson et al. |
| 6,190,893 B1 * | 2/2001 | Shastri et al. ............ 435/173.8 |
| 6,287,606 B1 * | 9/2001 | Bockman et al. ........... 424/650 |

OTHER PUBLICATIONS

Fujishige et al., "Alteration of cGMP Metabolism During Chondrogenic Differentiation of Chondroprogenitor-like EC Cells, ATDC5," *Biochim. Biophys. Acta*, 1452:219-227 (1999). Abstract Only.

Williams et al., "Tamoxifen Inhibits Phorbol Ester Stimulated Osteoclastic Bone Resorption: An Effect Mediated by Calmodulin," *Biochem. Cell Biol.*, 75:725-723 (2000). Abstract Only.

International Search Report. PCT/US02/41440, United States Patent Office as International Examining Authority.

* cited by examiner

*Primary Examiner*—Gary Kunz
*Assistant Examiner*—Mina Haghighatian
(74) *Attorney, Agent, or Firm*—Marshall, Gerstein & Borun LLP

(57) ABSTRACT

The present invention provides methods and compositions for promoting bone regeneration, comprising administration of calmodulin. The method of bone regeneration is applied to subjects having bone disorders characterized by decreased bone mass such as osteopenia and osteoporosis, as well as those suffering from non-union fractures.

11 Claims, No Drawings

USE OF CALMODULIN TO PROMOTE BONE REGENERATION

FIELD OF INVENTION

This application claims benefit of U.S. Provisional Patent Application 60/349,163 filed Jan. 16, 2002. The present invention relates to a method of promoting bone regeneration and treating symptoms of a bone disorder comprising administering calmodulin.

BACKGROUND

The remodeling of bone is an ongoing process consisting of bone formation and bone resorption. In healthy subjects, there is a normal balance between bone formation and bone resorption which maintains skeletal mass. Most of the bone surfaces are not active, i.e., are not involved in either bone formation or resorption, instead, there are active surfaces distributed randomly throughout the skeletal system where formation and resorption are locally coupled as units. Resorption areas are covered by osteoclasts, which are cells that resorb and remove osseous tissue, and bone formation surfaces are covered by active osteoblasts, which are cells that form osseous tissue.

Bone disorders affect millions of individuals everyday causing painful and debilitating symptoms including bone fractures. Of particular interest are bone disorders that are caused by abnormal osseous tissue homeostasis, which eventually leads to a loss of bone mass. The abnormal osseous tissue homeostasis is the result of an imbalance between bone formation by osteoblasts and bone resorption by osteoclasts that leads to a net bone resorption. The resulting decreased bone mass can lead to many different bone disorders, including osteopenia, osteoporosis, and other well known bone disorders.

One particular bone disorder, osteoporosis, is commonly observed in postmenopausal women and in the elderly and is characterized by, low bone mass and microarchitectural disruption that results in fractures with minimal trauma. Low bone mass is caused by an abnormality or disturbance in calcium homeostasis. Subjects afflicted with osteoporosis often experience fractures of the wrist and spine, and femoral fractures are common with respect to the elderly. The pathology of this disease is understood to involve a number of physical, hormonal, and nutritional factors acting alone or in combination.

Available treatment for osteoporosis is limited to improvement of dietary intake and physical activity, or use of pharmacological agents that reduce the net resorption of calcium from bone. The reduction of net resorption can be achieved either by decreasing the rate of bone resorption or by promoting bone formation. Current drugs available for osteoporosis therapy operate by preventing or inhibiting bone resorption, but this therapy has natural limitations as bone metabolism reaches a steady-state level. Once the steady-state level is achieved, there is no further increase in bone formation and bone mass density reaches a plateau. Existing anti-resorption agents useful in treating osteoporosis or increasing bone mass density include: calcium salts, e.g., calcium carbonate, vitamin D and its analogs, estrogen, calcitonin, and bisphosphonates. There are also bone-forming agents useful for treating osteoporosis and increasing bone mass density including fluoride, androgen, and parathyroid hormone. These agents have been found to be successful in maintaining bone mass density, but there is little success towards significantly improving the bone mass density in a subject with a bone disorder.

Another particular bone disease is a non-union fracture, which is a fracture which due to various factors fails to heal in a normal time period and requires some form of intervention to stimulate healing. Factors known to contribute to the occurrence of non-union fracture include smoking, diabetes and age. While some non-invasive treatments exist for this disorder, e.g., electrical stimulation or specialized braces, the treatments may not always be applicable to the particular fracture and even when applicable, may not result in success. Other treatments involve invasive measures, i.e., some type of surgery, such as removal of dead tissue, insertion of internal brace (either a rod, plate or screw), or bone graft. In some cases amputation may be necessary to prevent further injury to a subject presenting with a non-union fracture. Even if such intervention provides some success, the existing intervening treatments are typically inconvenient, expensive, often times painful, and can result in physical scarring or impairment.

Calmodulin is a calcium-dependent regulator protein that functions as an intracellular intermediary for calcium ions and is known to activate a number of enzymes involved in fundamental cell processes, e.g., protein phosphorylation, contractile processes, and metabolism of cyclic nucleotides, glycogen and calcium, as well as in other metabolic reactions. Calmodulin can also act as a 3'5'-cyclic nucleotide phosphodiesterase, which hydrolyzes the phosphodiester bond of a 3'5'-cyclic nucleotide to form the corresponding nucleotide.

There still remains a need for a treatment or preventive measure to increase the bone mass density in a subject suffering from a bone disorder, particularly osteoporosis. Further still, there remains a need for a treatment to heal non-union fractures without the need for invasive measures or amputation.

SUMMARY OF INVENTION

The present invention is directed to a method of promoting bone regeneration in a subject having a bone disorder or otherwise in need thereof, comprising administration of calmodulin in an amount effective to promote bone regeneration. The method of promoting bone regeneration can be applied to a subject suffering from a bone disorder characterized by decreased bone mass, particularly osteoporosis and osteopenia. The calmodulin may be administered through a number of common methods of administration including orally, intravenously, and subcutaneously. Preferably, the calmodulin is administered orally, particularly through sublingual mode of administration. More preferably, the calmodulin is administered as a daily dose ranging from about 0.1 units to about 1000 units. Still more preferably, the calmodulin is administered as a daily dose ranging from about 1 unit to about 100 units. In another more preferable embodiment, the subject is human and the calmodulin is administered as a daily dose ranging from about 20 units to about 80 units.

An aspect of the present invention is the method of promoting bone regeneration, wherein the subject is suffering from a non-union bone fracture. The calmodulin may be administered through a number of common methods of administration including orally, intravenously, and subcutaneously. Preferably, the calmodulin is administered sublingually. More preferably, the calmodulin is administered as a daily dose ranging from about 0.1 units to about 1000 units. Still more preferably, the calmodulin is administered as a daily dose ranging from about 1 unit to about 100 units. In another more preferable embodiment, the subject is a human and the calmodulin is administered sublingually as a daily dose ranging from about 20 units to about 80 units.

The present invention also provides a pharmaceutical composition useful for promoting bone regeneration in a subject in need thereof, comprising calmodulin in a pharmaceutically acceptable diluent. Preferably, the pharmaceutical composition is an oral dosage form with about 0.1 units to about 1000 units of calmodulin. In another preferred embodiment, the pharmaceutical composition is an oral dosage form with about 1 unit to about 100 units of calmodulin. In yet another preferable embodiment, the pharmaceutical composition is an oral dosage form with about 10 units to about 80 units of calmodulin.

Numerous other aspects and advantages of the present invention will be apparent upon consideration of the following detailed description, which describes preferred embodiments of the present invention and is not meant to limit the scope of the present invention.

DETAILED DESCRIPTION

The present invention provides methods for promoting bone regeneration through the administration of calmodulin.

The term "bone regeneration" is used herein to refer to an increase in bone mass, particularly using the methods described herein. The bone mass is increased by either increasing bone formation by osteoblasts, reducing bone resorption by osteoclasts, or both.

The term "bone disorder" is used herein to refer to bone disorders that are caused by decreased bone mass in addition to non-union fractures. The decreased bone mass is the result of abnormal osseous tissue homeostasis. Specifically, the abnormal homeostasis is either increased bone resorption by osteoclasts, reduced bone formation by osteoblasts, or both, which results in a net loss in bone mass.

The term "non-union fracture" is used herein to refer to a type of fracture that fails to heal in a normal time period and requires some form of intervention to stimulate healing. The methods described herein represent forms of intervention that can be used to treat non-union fractures, i.e., promote bone fusion at the point of fracture.

The term "effective amount" or "amount effective to promote bone regeneration" is used herein to refer to the amount of calmodulin administered to a subject to increase the bone density of the subject by causing a net generation of bone mass. This increase in bone mass or bone density can be due to either an increase in new bone formation or a decrease in bone resorption, or both, such that the net effect is an overall increase in bone mass or density.

Bone diseases associated with reduced bone mass can be prevented according to the methods described herein. Osteopenia and osteoporosis result from the ongoing loss of bone mass due to an imbalance in osseous tissue homeostasis. The imbalance causes a net loss in bone mass and over time leads to a loss of bone mass or skeletal atrophy. This overall loss in bone mass can be prevented or significantly reduced by ongoing treatment with calmodulin. Subjects with high risk for these bone diseases, such as the elderly and post-menopausal women, can be given a regimen of calmodulin to delay or prevent the onset of such bone diseases.

Calmodulin derived from any source, including without limitation from recombinant and non-recombinant sources, may be administered to a subject in need, by itself, or in pharmaceutical compositions where it is mixed with suitable carriers or excipient(s) at doses to treat or ameliorate a variety of disorders. Such a composition may optionally contain (in addition to calmodulin and a carrier) diluents, fillers, salts, buffers, stabilizers, solubilizers, and other materials well known in the art. The term "pharmaceutically acceptable" means a non-toxic material that does not interfere with the effectiveness of the biological activity of calmodulin. The characteristics of the carrier will depend on the route of administration.

The pharmaceutical composition may further contain other agents which either enhance the activity of the calmodulin or complement its activity or use in treatment, which include calcium and calcium salts. Such additional factors and/or agents may be included in the pharmaceutical composition to produce a synergistic effect with calmodulin or to minimize side effects.

Techniques for formulation and administration of the compounds of the instant application may be found in "Remington's Pharmaceutical Sciences," Mack Publishing Co., Easton, Pa., latest edition. A therapeutically effective dose further refers to that amount of the compound sufficient to result in promotion of bone regeneration leading to increased bone mass.

Suitable routes of administration may, for example, include oral, e.g., sublingual, buccal, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of calmodulin used in the pharmaceutical composition or to practice the method of the present invention can be carried out in a variety of conventional ways, such as oral ingestion, sublingual application, inhalation, topical application or cutaneous, subcutaneous, intraperitoneal, parenteral or intravenous injection. Sublingual administration to the subject is preferred.

Alternately, one may administer the compound in a local rather than systemic manner, for example, via injection of the compound directly into a localized area identified as containing problematic bone tissue, often in a depot or sustained release formulation. Also, one may administer the drug in a targeted drug delivery system, for example, in a liposome coated with a specific antibody, targeting, for example, bone tissue. The liposomes will be targeted to and taken up selectively by the afflicted tissue.

Pharmaceutical compositions for use in accordance with the present invention thus may be formulated in a conventional manner using one or more physiologically acceptable carriers comprising excipients and auxiliaries which facilitate processing of the calmodulin into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of calmodulin is administered orally, the calmodulin will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% calmodulin, and preferably from about 25 to 90% calmodulin. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of calmodulin, and preferably from about 1 to 50% calmodulin.

When a therapeutically effective amount of calmodulin is administered by intravenous, cutaneous or subcutaneous injection, the calmodulin will be in the form of a pyrogen-free, parenterally acceptable aqueous solution. The preparation of such parenterally acceptable calmodulin solutions, having due regard to pH, isotonicity, stability, and the like, is within the skill in the art. A preferred pharmaceutical composition for intravenous, cutaneous, or subcutaneous injection should contain, in addition to calmodulin, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the calmodulin with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained using a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of calmodulin doses.

Pharmaceutical preparations which can be used orally include push-fit capsules made of gelatin, as well as soft, sealed capsules made of gelatin and a plasticizer, such as glycerol or sorbitol. The push-fit capsules can contain the calmodulin in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Pharmaceutical formulations for parenteral administration include aqueous solutions of the calmodulin in water-soluble form. Additionally, suspensions of the calmodulin may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the calmodulin may be in powder form for constitution with a suitable vehicle, e.g., sterile pyrogen-free water, before use.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The amount of calmodulin in the dosage form of the pharmaceutical composition of the present invention will depend upon the nature and severity of the condition being treated, and on the nature of prior treatments which the subject has undergone. Ultimately, the attending physician will decide the amount of calmodulin with which to treat each individual subject. Initially, the attending physician will administer low doses of calmodulin and observe the subject's response. Larger doses of calmodulin may be administered until the optimal therapeutic effect is obtained for the subject, and at that point the dosage is not increased further. The decided amount of the dosage form of the pharmaceutical compositions used to practice the method of the present invention should contain about 0.1 units to about 1000 units of calmodulin, and preferably about 1 unit to about 100 units of calmodulin. More preferably, the various pharmaceutical compositions of the present invention should contain about 10 units to about 80 units of the calmodulin.

The therapeutic compositions are also presently valuable for veterinary applications. Particularly domestic animals and thoroughbred horses, in addition to humans, are desired subjects for such treatment with calmodulin. The dosage regimen of a calmodulin-containing pharmaceutical composition to be used in promoting bone regeneration will be determined by the attending physician considering various factors which modify the action of the calmodulin, e.g., the site of damage, the condition of the damaged bone, the subject's age, sex, and diet, time of administration and other clinical factors. Progress can be monitored by periodic assessment of bone growth and/or repair, for example, X-rays, histomorphometric determinations and tetracycline labeling.

EXAMPLES

The following examples describe specific embodiments of the present invention in the form of subjects experiencing increases in bone mass density as a result of calmodulin treatment. Example 1 describes treatment of a subject experiencing fractures in the ankle and diagnosed with osteopenia by administering calmodulin. Example 2 describes the treatment of a subject diagnosed with osteoporosis by administering calmodulin. Example 3 describes the treatment of a subject diagnosed with osteoporosis by administering calmodulin. Example 4 describes the treatment of a subject diagnosed with osteoporosis by administering calmodulin. Example 5 describes the treatment of a subject diagnosed with osteoporosis by administering calmodulin. Example 6 describes the treatment of a dog diagnosed with non-union fracture by administering calmodulin. Example 7 describes the treatment of a human diagnosed with non-union fracture by administering calmodulin. Example 8 describes treatment of a diabetic suffering from Charcot's joint of the right ankle.

Example 1

According to this example, a subject suffering from osteopenia was treated by sublingual administration of calmodulin according to the present invention. Calmodulin of bovine origin was obtained from Sigma, St. Louis. The subject was a 73 year old white female subject with no family history of kidney stones or osteoporosis, but has experienced fractured ankles and rheumatoid arthritis. The subject was administered calmodulin by sublingual administration at a dose of 14 units three times daily. In addition to the calmodulin, the subject was taking calcium supplements. Bone scans of the Hip-Ward's Triangle, Hip-Neck, Hip-Total, and Lumbar (L1–L4) were taken of the subject just prior to treatment and upon certain points during or upon completion of the calmodulin therapy.

A dual energy x-ray absorptiometry (DEXA) machine was used to take bone density measurements from subjects. The measurements are in the form of bone scans that provide a graphic output which can be analyzed. Specific areas on the graphic output were measured by a computer. A central site of the subject that was measured was the Ward's triangle, which is an area of diminished density in the trabecular pattern of the neck of the femur evident by x-ray as well as by direct inspection. Other central sites of the subject that were measured were the Hip-Neck, Hip-Total, and the Lumbar, particularly from L1–L4. A bone scan of these specific areas on a subject were taken at the time the calmodulin treatment was initiated, and another scan was taken of the same areas at a different point of time, either during or upon completion of the therapy. The data from the latter scans were compared to data from the initial bone scan according to the respective areas measured and comparisons were made to determine any changes in bone density at each of the areas measured.

For analysis of the progress of the subject to the calmodulin treatment, a bone scan was taken prior to calmodulin treatment and a second scan was taken after about a six month period of treatment. The results are in the form of three different types of measurements of bone density using the DEXA machine: T type, which represents the comparison in the bone density measurement to women's bone density at about age 20 years, which is when women's bone density normally peaks; Z type, which represents the comparison in the bone density measurement to the bone density of women of the same age as the subject; and bone mineral density type ("BMD"), which provides the weight of bone for a standard area in grams per square centimeter (g/cm$^2$). T and Z type measurements are in the units of standard deviations ("SD").

A clinical assessment of the health of a subject's bones from the SD values of T and Z type measurements can be seen in the following table.

| | Patient Compared to All Healthy Women | | |
|---|---|---|---|
| SD Value | % of Population with Lower Bone Density | % of Population with Higher Bone Density | Comment |
| +3.00 | 99.5 | 0.5 | Healthy Bone |
| +2.00 | 97.5 | 2.5 | Healthy Bone |
| +1.00 | 66 | 34 | Healthy bone, slight risk |
| 0.00 | 50 | 50 | Okay bone health, risk concerns |
| −1.00 | 34 | 66 | Fair bone health, some risk |
| −2.00 | 2.5 | 97.5 | Poor bone health |
| −3.00 | 0.5 | 99.5 | Very poor bone health |

Pursuant to World Health Organization ("WHO") criteria, a T score of 0 to −1.0 SD is considered a normal bone density measurement. Osteopenia is defined as a T score of −1.0 to −2.5. Osteoporosis is defined as any T score more negative than −2.5 SD or in the osteopenia defining range with fragility fractures of the hip or spine. Typically, 90% of subjects who develop fragility fractures have a BMD below −2.5 SD on T scores, which is called the fracture threshold. Those subjects with fragility fractures are considered as having severe osteoporosis.

In comparing multiple measurements, a same or more positive "T" or "Z" value shows an improvement in the progression of bone degenerations as the bone density is found to remain the same or actually improve over time. T value is understood in the art to be the most reliable predictor of fracture risk. Each one standard deviation decrease in bone mineral density at the lumbar spine increases the risk of fracture there one and a half-fold, and two-fold at the hip. An increase in the BMD value (or calcium density) shows that the subject is improving.

After a period of 6 months of continued treatment, the subject showed either similar or improved bone density (except slight worsening in Hip-Total) density as determined from the bone scan measurements shown in Table 1 below.

TABLE 1

| | Hip-Ward's Triangle | | | Hip-Neck | | | Hip-Total | | | Lumbar (L1–L4) | | |
|---|---|---|---|---|---|---|---|---|---|---|---|---|
| | T (SD) | Z (SD) | BMD (g/cm$^2$) | T (SD) | Z (SD) | BMD (g/cm$^2$) | T (SD) | Z (SD) | BMD (g/cm$^2$) | T (SD) | Z (SD) | BMD (g/cm$^2$) |
| Initial | −0.96 | +1.76 | +.622 | −0.89 | +1.08 | +0.751 | −0.54 | +1.13 | +0.877 | −1.35 | +0.93 | +0.899 |
| 6 Month | −0.97 | +1.78 | +.621 | −0.99 | +1.02 | +0.739 | −.065 | +1.05 | +0.862 | −0.75 | +1.57 | +0.964 |
| Change From Initial | −0.01 | +0.02 | −0.001 | −0.1 | −0.06 | −0.012 | −0.11 | −.08 | −0.015 | +0.6 | +0.64 | +0.065 |

Example 2

According to this example, a subject diagnosed with osteoporosis and hypertension was treated by sublingual administration of calmodulin according to the protocols of Example 1. The calmodulin was administered at a dose of 14 units three times daily. Bone scans were taken of various areas as described in Example 1 at a time prior to treatment and at times of about four and eleven months after treatment began.

The subject experienced either maintenance or improvement in bone density in different areas of the hip as determined from the bone scan measurements shown in Table 2 below. This was observed for both measurements taken at four months after treatment was initiated and at eleven months after treatment was initiated. Concurrently, there was a slight worsening in bone density in the Lumbar as signified by the measurements taken at eleven months after treatment was initiated the changes being T value (−0.21 SD) and Z value (−0.15 SD).

Example 4

According to this example, a subject diagnosed with osteoporosis, high blood pressure, and renal tubular stenosis was treated by sublingual administration of calmodulin according to the protocols in Example 1. The calmodulin was administered at a dose of 14 units three times daily. Bone scans were taken of various areas as described in Example 1 at a time prior to treatment and at times of about four and ten months after treatment began.

Either maintenance or significant improvements of bone health were seen in each measured area as determined from the bone scan measurements shown in Table 4 below.

TABLE 2

| | Hip-Ward's Triangle | | | Hip-Neck | | | Hip-Total | | | Lumbar (L1–L4) | | |
|---|---|---|---|---|---|---|---|---|---|---|---|---|
| | T (SD) | Z (SD) | BMD (g/cm$^2$) | T (SD) | Z (SD) | BMD (g/cm$^2$) | T (SD) | Z (SD) | BMD (g/cm$^2$) | T (SD) | Z (SD) | BMD (g/cm$^2$) |
| Initial | −2.88 | −0.19 | +0.397 | −2.53 | −0.58 | +0.569 | −1.15 | +0.50 | +802 | | −0.46 | +1.80 | +0.996 |
| 4 Month | −2.12 | +0.68 | +0.486 | −2.07 | −0.18 | +0.620 | −1.16 | +0.52 | +.801 | −0.48 | +1.80 | +0.994 |
| Change From Initial | +0.76 | +0.87 | +0.089 | +0.46 | +0.40 | +0.51 | −0.01 | −0.02 | −0.001 | −0.02 | 0 | −0.002 |
| 11 Month | −2.46 | −0.09 | +0.446 | −2.45 | −0.44 | +0.577 | −1.20 | +.50 | +.796 | −.67 | +1.65 | 0.973 |
| Change From Initial | +0.42 | +0.10 | +0.049 | +0.08 | +0.14 | +0.008 | −0.05 | 0.0 | −0.006 | −0.21 | −0.15 | −0.023 |

Example 3

According to this example, a subject diagnosed with osteoporosis, high blood pressure, and hypercholesterolemia was treated by sublingual administration of calmodulin according to the protocols of Example 1. The calmodulin was administered at a dose of 14 units three times daily. Bone scans were taken of various areas as described in Example 1 at a time prior to treatment and at times of about four and twelve months after treatment began. The subject experienced either maintenance or improvement in bone density in each of the measured areas as determined from the bone scan measurements shown in Table 3 below.

TABLE 3

| | Hip-Ward's Triangle | | | Hip-Neck | | | Hip-Total | | | Lumbar (L1–L4) | | |
|---|---|---|---|---|---|---|---|---|---|---|---|---|
| | T (SD) | Z (SD) | BMD (g/cm$^2$) | T (SD) | Z (SD) | BMD (g/cm$^2$) | T (SD) | Z (SD) | BMD (g/cm$^2$) | T (SD) | Z (SD) | BMD (g/cm$^2$) |
| Initial | −3.31 | −0.55 | +0.347 | −2.37 | −0.37 | +0.585 | −2.56 | −0.86 | +0.629 | −3.34 | −1.01 | +0.680 |
| 4 Month | −2.77 | +0.02 | +0.41 | −2.39 | −0.35 | +0.584 | −2.55 | −0.82 | −0.631 | −3.42 | −1.07 | +0.671 |
| Change From Initial | +0.54 | +0.57 | +0.063 | −0.02 | +0.02 | +0.001 | +0.01 | +0.04 | +0.002 | −0.08 | −0.06 | −0.009 |
| 12 Month | −3.24 | −0.42 | +0.355 | −2.29 | −0.22 | +0.595 | −2.51 | −0.74 | +0.636 | −3.24 | −0.87 | +0.689 |
| Change From Initial | +0.07 | +0.13 | +0.008 | +0.08 | +0.15 | +0.010 | +0.05 | +0.12 | +0.007 | +0.10 | +0.14 | +0.009 |

TABLE 4

| | Hip-Ward's Triangle | | | Hip-Neck | | | Hip-Total | | | Lumbar (L1–L4) | | |
|---|---|---|---|---|---|---|---|---|---|---|---|---|
| | T (SD) | Z (SD) | BMD (g/cm$^2$) | T (SD) | Z (SD) | BMD (g/cm$^2$) | T (SD) | Z (SD) | BMD (g/cm$^2$) | T (SD) | Z (SD) | BMD (g/cm$^2$) |
| Initial | −3.78 | −1.18 | +.291 | −3.14 | −1.28 | +501 | −2.64 | −1.08 | +620 | −3.28 | −1.11 | +686 |
| 4 Month | −3.42 | −0.79 | +334 | −3.20 | −1.33 | +.493 | −2.60 | −1.02 | +.626 | −3.26 | −1.07 | +.688 |
| Change From Initial | +0.36 | +0.39 | +.043 | −0.06 | −0.05 | −0.008 | −0.04 | +0.06 | +.006 | +0.02 | +0.04 | +.002 |

TABLE 4-continued

|  | Hip-Ward's Triangle | | | Hip-Neck | | | Hip-Total | | | Lumbar (L1–L4) | | |
| --- | --- | --- | --- | --- | --- | --- | --- | --- | --- | --- | --- | --- |
|  | T (SD) | Z (SD) | BMD (g/cm$^2$) | T (SD) | Z (SD) | BMD (g/cm$^2$) | T (SD) | Z (SD) | BMD (g/cm$^2$) | T (SD) | Z (SD) | BMD (g/cm$^2$) |
| 10 Month | −3.84 | −1.19 | +.285 | −3.30 | −1.39 | +.483 | −2.56 | −0.95 | +.630 | −3.33 | −1.11 | +681 |
| Change From Initial | −0.06 | −0.01 | −.006 | −0.16 | −0.11 | −.018 | +0.08 | +0.13 | +.010 | −0.05 | 0.0 | −.005 |

Example 5

According to this example, a subject diagnosed with osteoporosis and hypothyroidism was treated by sublingual administration of calmodulin according to the protocols in Example 1. The calmodulin was administered at a dose of 14 units three times daily. Bone scans were taken of various areas as described in Example 1 at a time prior to treatment and at times of about five and twelve months after treatment began.

Either maintenance or significant improvements of bone health were seen in each measured area as determined from the bone scan measurements shown in Table 5 below. Concurrently, there was slight worsening in the Hip-Neck in the T value (−0.80 SD and −0.15 SD, at 5 and 12 months, respectively) and the Z value (−0.92 SD and −0.11 SD, at 5 and 12 months, respectively) according to measurements made.

Example 8

Treatment of Charcot's Joint in a Human

According to this example, a 58-year old female subject suffering with type II diabetes for more than 15 years developed Charcot's joint of the right ankle characterized by deterioration of the joint followed shortly thereafter with Charcot's joint of the left ankle also characterized by deterioration of the joint. Charcot's joint which is also known as Neuropathic Osteoarthropathy and is associated with partial or total loss of sensation, bone deterioration, and in some cases bone breakage. The subject was given narcotics for pain, both legs were placed in casts and she was instructed to rest.

The subject was also treated by sublingual administration of calmodulin (14 units) four times daily. Five weeks after the initiation of calmodulin treatment, the subject's podia-

TABLE 5

|  | Hip-Ward's Triangle | | | Hip-Neck | | | Hip-Total | | | Lumbar (L1–L4) | | |
| --- | --- | --- | --- | --- | --- | --- | --- | --- | --- | --- | --- | --- |
|  | T (SD) | Z (SD) | BMD (g/cm$^2$) | T (SD) | 7 (SD) | BMD (g/cm$^2$) | T (SD) | 7 (SD) | BMD (g/cm$^2$) | T (SD) | 7 (SD) | BMD (g/cm$^2$) |
| Initial | −3.03 | −0.32 | +380 | −2.35 | −0.40 | +.588 | −1.21 | +0.45 | +.795 | −2.01 | +0.42 | +728 |
| 5 Month | −2.91 | −0.17 | +394 | −2.40 | −0.41 | +.582 | −1.05 | +0.64 | +.814 | −2.81 | −0.50 | +.738 |
| Change From Initial | +0.12 | +0.15 | +.014 | −0.05 | −0.01 | −.006 | +0.16 | +.0.19 | +019 | −0.80 | −0.92 | −.157 |
| 12 Month | −2.88 | −0.11 | −.397 | −2.32 | −0.3 | +.592 | −1.17 | +0.60 | +.806 | −2.16 | +0.31 | +.703 |
| Change From Initial | +0.15 | +0.21 | +.017 | +0.03 | +0.10 | +.004 | +0.04 | +0.15 | +0.11 | −0.15 | −0.11 | −.025 |

Example 6

Treatment of Non-Union Fractures in a Dog

According to this example, a dog that with a fractured limb that refused to heal, i.e., a non-union fracture, was treated by administration of calmodulin via subcutaneous injection according to the present invention. The fractured limb failed to heal after using normal treatments including immobilization with a splint and a cast. One dose (14 units) of calmodulin was administered subcutaneously twice daily. After a period of about 4–8 weeks, the fractured limb healed.

Example 7

Treatment of Non-Union Fractures in a Human

According to this example, a person with a fractured limb that refused to heal, i.e., a non-union fracture, was treated by administration of calmodulin via subcutaneous injection. The fractured limb failed to heal after using normal treatments including immobilization with a splint and a cast. One dose (14 units) of calmodulin was administered subcutaneously four times daily. After a period of about 4-8 weeks, the fractured limb was completely healed.

trist (having a specialty in treatment of diabetics) reported that he had "never seen such rapid resolution" of a subject.

The overall results of the calmodulin treatment on the bone disorders comprising osteoporosis and osteopenia exhibit a trend towards either maintenance or improvement in bone density. The present results must be viewed with the fact that the progression of these bone disorders occurs over extended periods of time, on the order of years. Accordingly, reversal of the damaging effects of these bone disorders, takes many years to achieve. The presently described examples show a reduction or elimination in disease progression over the time-course of up to one year, in addition to a reversal of the effects of the disease.

The invention has been described in terms of its preferred embodiments and is only intended to be limited by the scope of the following claims.

What is claimed is:

1. A method of promoting bone regeneration wherein calmodulin is administered at a daily dosage ranging from 0.1 units to about 1000 units in a subject in need thereof, comprising administration of calmodulin in an amount effective to promote bone regeneration.

2. The method of promoting bone regeneration of claim 1, wherein the subject is suffering from a bone disorder characterized by decreased bone mass.

3. The method of promoting bone regeneration of claim 2, wherein the bone disorder is osteoporosis or osteopenia.

4. The method of promoting bone regeneration of claim 2, wherein the calmodulin is administered sublingually or subcutaneously.

5. The method of promoting bone regeneration of claim 4, wherein the calmodulin is administered at a daily dosage ranging from about 1 unit to about 100 units.

6. The method of promoting bone regeneration of claim 4, wherein the subject is human and the calmodulin is administered as a daily dose ranging from about 20 units to about 80 units.

7. The method of promoting bone regeneration of claim 1, wherein the subject is suffering from a non-union bone fracture.

8. The method of promoting bone regeneration of claim 7, wherein the calmodulin is administered sublingually or subcutaneously.

9. The method of promoting bone regeneration of claim 8, wherein the calmodulin is administered at a daily dosage ranging from about 1 unit to about 100 units.

10. The method of promoting bone regeneration of claim 8, wherein the subject is a human and the calmodulin is administered at a daily dosage ranging from about 20 units to about 80 units.

11. The method of promoting bone regeneration of claim 8, wherein the subject is a dog and the calmodulin is administered as a daily dose ranging from about 10 units to about 40 units.

* * * * *